United States Patent

Van Bockstaele et al.

[11] Patent Number: 5,122,434
[45] Date of Patent: Jun. 16, 1992

[54] PHOTOGRAPHIC ROOMLIGHT MATERIALS CONTAINING HALOGEN ACCEPTORS

[75] Inventors: Marc H. Van Bockstaele, Mortsel; Marc B. Graindourze, Overpelt; Jean-Marie O. Dewanckele, Drongen, all of Belgium

[73] Assignee: AGFA-Gevaert, N.V., Mortsel, Belgium

[21] Appl. No.: 668,625

[22] Filed: Mar. 13, 1991

[30] Foreign Application Priority Data

Mar. 19, 1990 [EP] European Pat. Off. ........ 90200647.7

[51] Int. Cl.⁵ .............................................. G03C 1/06
[52] U.S. Cl. .................................. 430/264; 430/567; 430/606; 430/614
[58] Field of Search ................ 430/606, 567, 264, 614

[56] References Cited

U.S. PATENT DOCUMENTS

| | | | |
|---|---|---|---|
| 3,287,137 | 11/1966 | McBride | 430/599 |
| 3,502,471 | 3/1970 | Van Pee et al. | 430/614 |
| 4,912,017 | 3/1990 | Takagi et al. | 430/606 |
| 4,939,067 | 7/1990 | Takagi et al. | 430/606 |

OTHER PUBLICATIONS

Research Disclosure, Mar. 1973, Item 10723, pp. 29–30, Anonymous.

*Primary Examiner*—Charles L. Bowers, Jr.
*Assistant Examiner*—Thomas R. Neville
*Attorney, Agent, or Firm*—Breiner & Breiner

[57] ABSTRACT

A halogen acceptor according to general chemical formula (I) is added to a photographic negative roomlight emulsion, consisting of at least 90% of silver chloride, having an average grain size smaller than 0.3 micron, and internally doped with an element of group VIII of the periodic table.

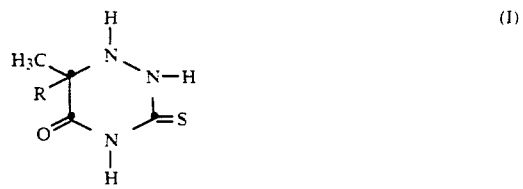

In this formula:

$R^1$ = alkyl having at least 4 C-atoms, preferably between 4 and 9.

In the coated emulsion layer, the halogen acceptors of the invention provide a clear print-out effect and an improved development latitude when the emulsion layer is developed in a "hard-dot Rapid Access" processing system.

In a preferred embodiment $R = -C_6H_{13}$ and the element of group VIII is Rhodium.

4 Claims, No Drawings

PHOTOGRAPHIC ROOMLIGHT MATERIALS CONTAINING HALOGEN ACCEPTORS

FIELD OF THE INVENTION

The present invention relates to halogen-accepting compounds and to photographic emulsion layers containing these compounds.

BACKGROUND OF THE INVENTION

In the sector of pre-press activity known as graphic and reprographic arts an intensive use is made of contact copying materials to reproduce screen dot images, line work and typesetting work. Both negative working photographic materials which produce negative-positive or positive-negative copies are used as well as so-called direct positive working materials giving rise to negative-negative or positive-positive reproductions.

In order to obtain exact copies with sharp dot and line edges, it is necessary to use fine-grained relatively insensitive photographic emulsions. The materials containing this type of emulsions are image-wise exposed in contact with the original in a graphic arts copying apparatus by means of high intensity radiation, preferably by light sources emitting a high content of near-ultraviolet light. Common light sources for this purpose are mercury vapour lamps, metal-halogen lamps, xenon tubes, pulsed xenon tubes and quartz-halogen sources.

The handling of ever increasing amounts of photographic materials of different kinds, the decentralisation of the distinct steps in the reproduction cycle etc., have created a demand for silver halide materials which can be handled under clear ambient light illumination. This demand has given rise to the development of so called "roomlight materials" which can be image-wise exposed, handled and processed without the occurence of fogging in a reasonable time while being illuminated by common office fluorescent tubes and daylight penetrating through office windows. Prior art material which can be handled under roomlight conditions has been described in e.g. U.S. Pat. No. 2,219,667 and GB 1,330,044.

A much appreciated photographic effect occuring with some commercially available roomlight materials is the so-called "print-out" effect. This phenomenon can be generally described as the darkening of photographic emulsions under the influence of extended exposure to radiation or of image-wise exposure to a high intensity source followed by a low intensity exposure if required. Depending on the application the print-out image can be further developed to the full metal silver density. Several commercial roomlight materials show a print-out effect after image-wise exposure by a common UV emitting light source. Since roomlight emulsion are handled in bright light, this print-out effect allows visual differentiation between exposed and non-exposed parts. This is much appreciated by the customer handling roomlight contact copying materials because it allows him to check before processing if an exposure has been made of the correct original and if it has been made at the correct dimensional position on the copying material sheet. The latter is most important in the case when successive exposures are to be made of several originals resulting in an assembly of copies on one roomlight material sheet. So it is clear that the presence of the print-out effect is an important aspect of convenient handling. However it is a disadvantage that with most present roomlight materials the print-out effect becomes clearly visible only after considerable overexposure.

Scientific reports on the print-out effect have been published in e.g. J. Photogr. Sci., Vol. 6, p. 141 (1958), J. Opt. Soc. Am., Vol. 28, p. 431 (1938), J. Chem. Phys., Vol. 18, p. 499 (1950), J. Opt. Soc. Am., Vol. 23, p. 157 (1933) and ibid., Vol. 26, p. 347 (1936). X-ray or electron diffraction demonstrate that silver metal is formed; so the print-out effect can be conceived as a latent image photolytically grown to visible dimensions. Analytical techniques show the release of halogen; so it is no wonder that so-called halogen acceptors can enhance the print-out effect. Suitable halogen acceptors which promote the print-out effect are disclosed e.g. in U.S. Pat. Nos. 3,287,137 and 3,364,032. The print-out effect can serve merely as a control method as it is the case with roomlight copying materials where a conventional development follows, or it can constitute the final image as it is the case e.g. in high speed oscillographic recording materials. Suitable halogen acceptors for this kind of application are e.g. perhydro-1,2 4-triazine-5-one-3-thione derivatives disclosed in U.S. Pat. No. 3,502,471.

Another aspect of convenient handling for the consumer of roomlight materials, apart from the print-out effect, is the presence of sufficient development latitude. One way of defining the development latitude is the development time interval, expressed as maximal procentual deviation from the ideal development time, in which the sensitometric properties and the screen dot quality remain at an acceptable level.

In the pre-press graphic arts field one can distinguish three major groups of processing systems. Widely used are the so-called Rapid Access systems (type 1) which employ a superadditive mixture of two developing agents e.g. hydrochinon and 1-phenyl-3-pyrazolidinone or hydrochinon and N-methyl-p-aminophenol; they contain sufficient sulphite ions to provide for stable developer solutions, resistant to exhaustion and aerial oxidation. An additional advantage is their broad development latitude. However these systems do not provide for superior dot quality and are restricted to those applications where superior dot quality is not utmost important. Another classical processing systems group comprises the so-called "lith developers" containing hydrochinon as sole developing agent and a low sulphite concentration (type 2), which produce excellent dot quality but are more expensive and less stable and therefor require sophisticated regeneration methods in order to compensate for exhaustion and aerial oxidation. Of recent years a third group of graphic arts processing systems came into existence combining the advantages of type 1 and type 2 (stability and dot quality). This new, so-called "hard-dot Rapid Access" systems combine a high sulphite content with a mechanism in which a chemical speices is sufficiently active to initiate an infectious development or an infectious development-like high-contrast development. Possible mechanisms can be based on, but are not restricted to hydrazine, hydrochinon or tetrazolium salt chemistries. These systems have the superior quality of classical "lith" systems in addition to the good chemical stability of the conventional Rapid Access systems. Examples of these type 3 developing systems and compatible materials are marketed by EASTMAN KODAK Co under the trade name ULTRATEC, by FUJI PHOTO Ltd under the trade name GRANDEX and by AGFA under the trade name AGFASTAR. An example of a developer as used in the latter system contains essentially hydrochinon as sole developing agent, sufficient sulphite ions comparable to type 1 developers, a nitroindazole derivative, a polyalkyleneoxide polymer and an inorganic alkali, as disclosed e.g. in U.S. Pat. No. 4,710,451.

When using graphic arts emulsions containing bromide as major halide the development latitude is very large (from about 10 to 60 seconds) in type 1 developers. In lith type developers (type 2) this latitude is reduced to about 10% which is no easy-to-handle situation. On the contrary, in type 3 developers a satisfying situation of about 50% development latitude has been restored. However for roomlight applications the emulsion designer tends to prefer silver chloride emulsions which become less easy fogged under ambient light conditions than bromide emulsions thanks to their spectral sensitivity which has its maximal value in the near ultraviolet and extends less in the visible spectral region than it is the case with bromide emulsions. However silver chloride emulsions tend to develop faster than silver bromide emulsions particularly in "hard-dot Rapid Access" developers. So for the convenience of compatibility of development time of both chloride and bromide emulsions in the same processing sequence, development restrainers have to be added to silver chloride emulsions. However these development restrainers show the disadvantage of strongly reducing the development latitude especially in developers of type 3.

It is the object of the present invention to overcome this problem of reduced development latitude when roomlight materials are processed in "hard-dot Rapid Access" developers.

It is a further object of the present invention to realise graphic arts photographic roomlight materials which exhibit a clear print-out effect, not only at overexposure but at the correct exposure to reproduce exactly a 50% screen dot.

SUMMARY OF THE INVENTION

The objects of this invention are realised by adding to a photographic negative roomlight emulsion, consisting of at least 90 mole % of silver chloride, having an average grain size smaller than 0.3 micrometer, and internally doped with a compound containing an element of group VIII of the periodic table, an halogen acceptor represented by following general formula (I):

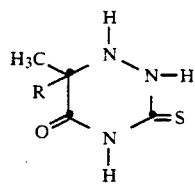

wherein:

R = alkyl having at least 4 C-atoms, preferably between 4 and 9.

It was suprisingly found that the addition of the compounds according to formula (I), apart from provoking a desired print-out effect, assures a sufficient development latitude when the coated roomlight emulsion is image-wise exposed and developed in a "hard-dot Rapid Access" processing system. Moreover this is accomplished without negatively influencing the photographic properties of the coated emulsion when developed in a conventional Rapid Access developer of type 1.

DETAILED DESCRIPTION OF THE INVENTION

Specific examples of halogen acceptors according to the invention include following compounds I-1, I-2 and I-3; comparison compounds include C-1 and C-2:

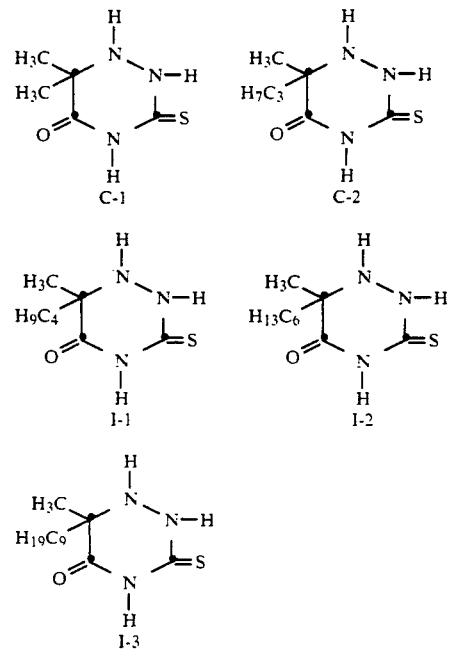

The halogen acceptors of the present invention are present in the light sensitive layer(s) of the photographic material and are adsorbed on the surface of the silver halide grains. The silver halide emulsion(s) can be present in a single layer or in a multi-layer pack, e.g. a double layer. Preferably the halogen acceptors are present in a concentration ranging from $10^{-5}$ mole to $10^{-2}$ mole per mole of silver halide.

The negative working roomlight emulsions used in the invention consist of at least 90 mole % of silver chloride. The rest percentage of the halide can be bromide or a mixture of bromide and minor amounts of iodide. They can be prepared from soluble silver salts and soluble halides according to different methods as described e.g. by P. Glafkides in "Chimie et Physique Photographique", Paul Montel, Paris (1967), by G. F. Duffin in "Photographic Emulsion Chemistry", The Focal Press, London (1966), and by V. L. Zelikman et al in "Making and Coating Photographic Emulsion", The Focal Press, London (1966). The silver halide can be precipitated according to the single-jet method, the double-jet method, or a more complex method. Preferably they are prepared by a simple double jet method. Their average grain size is limited to maximally 0.30 micrometer.

The emulsions are doped with a group VIII element, e.g. $Rh^{3+}$ ions by the presence during precipitation of a soluble compound containing the group VIII element, e.g. sodium hexachlororhodate, in a concentration ranging from $10^{-6}$ to $10^{-2}$ mole per mole of silver halide.

The emulsion can be desalted in the usual ways e.g. by dialysis, by flocculation and re-dispersing, or by ultrafiltration.

The roomlight emulsions can be chemically sensitized or not. In the affirmative case they can be chemically ripened as described i.a. in the above-mentioned "Photographic Emulsion Chemistry" by G. F. Duffin, in the above-mentioned "Making and Coating Photographic Emulsion" by V. L. Zelikman et al, and in "Die Grundlagen der Photographischen Prozesse mit Silberhalogeniden" edited by H. Frieser and published by Akademische Verlagsgesellschaft (1968). As described in said literature chemical sensitization can be carried out by effecting the ripening in the presence of small amounts of compounds containing sulphur e.g. thiosulphate, thiocyanate, thioureas, sulphites, mercapto compounds, and rhodamines. The emulsions can be sensitized also by means of gold-sulphur ripeners or by means of reductors e.g. tin compounds as described in GB 789,823, amines, hydrazine derivatives, formamidine-sulphinic acids, and silane compounds.

Apart from the halogen acceptors of the present invention, the emulsion layer may comprise several other compounds, e.g. substances preventing the formation of fog or stabilizing the sensitometric characteristics during storage. Many known compounds can be added as fog-inhibiting agent, stabilizer or development restrainer to the silver halide emulsion. Suitable examples are i.a. benzothiazolium salts, chlorobenzimidazoles, bromobenzimidazoles, mercaptothiazoles, mercaptobenzothiazoles, mercaptobenzimidazoles, mercaptothiadiazoles, aminotriazoles, benzotriazoles, (preferably 5-methyl-benzotriazole), mercaptotetrazoles, in particular 1-phenyl-5-mercapto-tetrazole, mercaptopyrimidines, mercaptotriazines, benzothiazoline-2-thione, oxazoline-thione, triazaindenes, tetrazaindenes and pentazaindenes, especially those described by Birr in Z. Wiss. Phot. 47 (1952), pages 2-58, triazolopyrimidines such as those described in GB 1,203,757, GB 1,209,146, JA-Appl. 75-39537, and GB 1,500,278, and 7-hydroxy-s-triazolo-[1,5-a]-pyrimidines as described in U.S. Pat. No. 4,727,017, and other compounds such as benzenethiosulphonic acid, benzenethiosulphinic acid and benzenethiosulphonic acid amide. These substances can be added to the silver halide emulsion prior to, during, or after the ripening thereof and mixtures of two or more of these compounds can be used.

Besides the light sensitive emulsion layer(s) the photographic material can contain several non light sensitive layers, e.g. a protective top layer, one or more backing layers, and one or more intermediate layers eventually containing filter or antihalation dyes which absorb scattering light and thus promote the image sharpness. Suitable light-absorbing dyes are described in e.g. U.S. Pat. No. 4,092,168, U.S. Pat. No. 4,311,787, DE 2,453,217, and gB 7,907,440. One or more backing layers can be provided at the non-light sensitive side of the support. These layers which can serve as anti-curl layers can contain i.a. matting agents e.g. silica particles, lubricants, antistatic agents, light-absorbing dyes, opacifying agents, e.g. titanium oxide and the usual ingredients like hardeners and wetting agents.

Besides the silver halide another essential component of a light-sensitive emulsion layer is the binder. The binder is a hydrophilic colloid, preferably gelatin. Gelatin can, however, be replaced in part or integrally by synthetic, semi-synthetic, or natural polymers. Synthetic substitutes for gelatin are e.g. polyvinyl alcohol, poly-N-vinyl-pyrrolidone, polyvinyl-imidazole, polyvinyl-pyrazole, polyacrylamide, polyacrylic acid, and derivatives thereof, in particular copolymers thereof.

Natural substitutes for gelatin are e.g. other proteins such as zein, albumin and casein, cellulose, saccharides, starch, and alginates. In general, the semi-synthetic substitutes for gelatin are modified natural products e.g. gelatin derivatives obtained by conversion of gelatin with alkylating or acylating agents or by grafting of polymerizable monomers on gelatin, and cellulose derivatives such as hydroxyalkyl cellulose, carboxymethyl cellulose, phthaloyl cellulose, and cellulose sulphates.

The binder should dispose of an acceptable high number of functional groups, which by reaction with an appropriate hardening agent can provide a sufficiently resistant layer. Such functional groups are especially amino groups, but also carboxylic groups, hydroxy groups, and active methylene groups.

The gelatin can be lime-treated or acid-treated gelatin. The preparation of such gelatin types has been described in e.g. "The Science and Technology of Gelatin", edited by A.G. Ward and A. Courts, Academic Press 1977, page 295 and next pages. The gelatin can also be an enzyme-treated gelatin as described in Bull. Soc. Sci. Phot. Japan, N. 16, page 30 (1966).

The binders of the photographic element, especially when the binder used is gelatin, can be hardened with appropriate hardening agents such as those of the epoxide type, those of the ethylenimine type, those of the vinylsulfone type e.g. 1,3-vinylsulphonyl-2-propanol, chromium salts e.g. chromium acetate and chromium alum, aldehydes e.g. formaldehyde, glyoxal, and glutaraldehyde, N-methylol compounds e.g. dimethylolurea and methyloldimethylhydantoin, dioxan derivatives e.g. 2,3-dihydroxy-dioxan, active vinyl compounds e.g. 1,3,5-triacryloyl-hexahydro-s-triazine, active halogen compounds e.g. 2,4-dichloro-6-hydroxy-s-triazine, and mucohalogenic acids e.g. mucochloric acid and mucophenoxychloric acid. These hardeners can be used alone or in combination. The binders can also be hardened with fast-reacting hardeners such as carbamoylpyridinium salts as disclosed in U.S. Pat. No. 4,063,952.

The photographic element of the present invention may further comprise various kinds of surface-active agents in the photographic emulsion layer or in at least one other hydrophilic colloid layer. Suitable surface-active agents include non-ionic agents such as saponins, alkylene oxides e.g. polyethylene glycol, polyethylene glycol/polypropylene glycol condensation products, polyethylene glycol alkyl ethers or polyethylene glycol alkylaryl ethers, polyethylene glycol esters, polyethylene glycol sorbitan esters, polyalkylene glycol alkylamines or alkylamides, silicone-polyethylene oxide adducts, glycidol derivatives, fatty acid esters of polyhydric alcohols and alkyl esters of saccharides; anionic agents comprising an acid group such as a carboxy, sulpho, phospho, sulphuric or phosphoric ester group; ampholytic agents such as aminoacids, aminoalkyl sulphonic acids, aminoalkyl sulphates or phosphates, alkyl betaines, and amine-N-oxides; and cationic agents such as alkylamine salts, aliphatic, aromatic, or heterocyclic quaternary ammonium salts, aliphatic or heterocyclic ring-containing phosphonium or sulphonium salts. Such surface-active agents can be used for various purposes e.g. as coating aids, as compounds preventing electric charges, or improving slidability. Preferred surface-active coating agents are compounds containing perfluorinated alkyl groups.

The photographic element of the present invention may further comprise various other additives such as e.g. compounds improving the dimensional stability of the photographic element, UV-absorbers, spacing agents, and plasticizers.

Suitable additives for improving the dimensional stability of the photographic element are i.a. dispersions of a water-soluble or hardly soluble synthetic polymer e.g. polymers of alkyl(meth)acrylates, alkoxy(meth)acrylates, glycidyl (meth)acrylates, (meth)acrylamides, vinyl esters, acrylonitriles, olefins, and styrenes, or copolymers of the above with acrylic acids, methacrylic acids, Alpha-Beta-unsaturated dicarboxylic acids, hydroxyalkyl (meth)acrylates, sulphoalkyl (meth)acrylates, and styrene sulphonic acids. These compounds can be present in the light sensitive or non light sensitive layers; in the case of multiple light sensitive layers they can be present in one or more of them.

The support of the photographic material may be opaque or transparent, e.g. a paper support or resin support. When a paper support is used preference is given to one coated at one or both sides with an Alpha-olefin polymer, e.g. a polyethylene layer which optionally contains an anti-halation dye or pigment. It is also possible to use an organic resin support e.g. cellulose nitrate film, cellulose acetate film, poly(vinyl acetal) film, polystyrene film, poly(ethylene terephthalate) film, polycarbonate film, polyvinylchloride film or poly-Alpha-olefin films such as polyethylene or polypropylene film. The thickness of such organic resin film is preferably comprised between 0.07 and 0.35 mm. These organic resin supports are preferably coated with a subbing layer which can contain water insoluble particles such as silica or titanium dioxide.

The photographic material containing the halogen acceptors of the invention can be exposed to any usual light source for roomlight materials, e.g. mercury vapour lamps, metal-halogen lamps, xenon tubes, pulsed xenon tubes and quartz-halogen sources. They can be processed in any developer but the full benifit of the present invention only becomes apparent when "hard-dot Rapid Access" processing systems are used. After development the materials are fixed in a conventional thiosulphate containing fixer, washed and dried. Preferably the processing cycle occurs in an automatically operating apparatus such as a RAPILINE, marketed by AGFA.

The following example illustrates the present invention without however being limited to it.

EXAMPLE 1

Synthesis of 6-hexyl-6-methyl-perhydro-1,2,4-triazine-5-one-3-thione.

A solution of potassium cyanide (45 g; 0.7 mole) in water (75 ml) was slowly added to a cold (0° C.) suspension of thiosemicarbazide (9.1 g; 0.1 mole) in a mixture of acetic acid (48 ml; 0.8 mole), water (40 ml) and ethanol (40 ml). Next, octanone-2 (12.8 g; 0.1 mole) was added. The suspension was then heated at 70° C. and stirred for two hours. An oily layer separated upon cooling. Crystallization occurred after cooling in an ice-bath. The precipitate was filtered off and washed with water. Recrystallization from toluene gave intermediate compound 1-(2-cyano-octyl-2)-thiosemicarbazide. Yield: 63.1%; melting point: 102° C.

A suspension of this intermediate compound (15 g; 0.066 mole) in concentrated hydrochloric acid (37%: 78.5 ml) was stirred at 80° C. for 2 hours. The mixture was cooled to ambient temperature and poured in water (500 ml). The precipitate was filtered, washed with water and dried. Recrystallization from isopropanol (50 ml) gave pure 6-hexyl-6-methyl-perhydro-1,2,4-triazine-5-one-3-thione. Yield: 33%; melting point: 150° C.

EXAMPLE 2

A cubic negative roomlight emulsion consisting of 100 mole % of chloride having an average grain size of 0.20 micrometer and doped with $1 \times 10^{-4}$ mole $Rh^{3+}$ per mole of silver chloride was prepared by a double jet precipitation method. A chemical ripening was performed using $2 \times 10^{-5}$ mole sodium thiosulphate and $2.5 \times 10^{-6}$ chloroauric acid. The emulsion was divided in several aliquot portions and to each portion halogen acceptors were added (see table 1). The emulsions were coated at 5.7 g/m² of silver halide, expressed as $AgNO_3$, using conventional coating aids and the di-sodium salt of 1-[3-(2-sulfobenzamido)]-phenyl-5-mercapto-tetrazole as development restrainer. The coated emulsions were exposed by a 1000 Watt mercury vapour lamp. The development proceeded at 38° C. for different times in a solution having the following composition:

| | |
|---|---|
| sodium carbonate | 40 g |
| sodium bromide | 4 g |
| sodium sulphite | 70 g |
| hydroquinone | 40 g |
| N-methylformamide | 30 ml |
| 5-nitroindazole | 75 mg |
| polyoxyethylene glycol (average number of oxyethylene units being 70) | 200 mg |
| water up to pH adjusted to 11.5 with sodium hydroxide | 1 l |

Table 1 presents the results of print-out effect and development latitude.

TABLE 1

| Halogen-acceptor | concentration[1] | print-out[2] | development-latitude[3] | note |
|---|---|---|---|---|
| — | — | 0 | <20% | comparison |
| C-1 | 1.75 × 10⁻³ | 7 | <15% | comparison |
| C-2 | 2.50 × 10⁻³ | 7 | <15% | comparison |
| " | 5.00 × 10⁻³ | 8 | <15% | comparison |
| I-1 | 2.25 × 10⁻³ | 7 | 20% | invention |
| " | 4.50 × 10⁻³ | 8 | 20% | invention |
| I-2 | 4.12 × 10⁻⁴ | 5 | 35% | invention |
| " | 1.25 × 10⁻³ | 7 | 40% | invention |
| " | 2.50 × 10⁻³ | 8 | >50% | invention |
| " | 4.12 × 10⁻³ | 10 | 30% | invention |
| I-3 | 1.10 × 10⁻³ | 6 | 25% | invention |
| " | 2.20 × 10⁻³ | 7 | 40% | invention |
| " | 3.70 × 10⁻³ | 7 | 30% | invention | notes:
[1] expressed in mole per mole of silver halide;
[2] evaluated at an exposure corresponding to an exact reproduction of a 50% dot screen original: the effect is evaluated in arbitrary units ranging from no print-out (0) to a clear distinct image (10);
[3] the development latitude is defined as the development time interval, expressed as maximal procentual deviation from the ideal development time, in which there is maintenance of hard-dot quality when contact exposed through a continuous tone wedge combined with a gray negative screen with a screen ruling of 54 lines/cm.

We claim:

1. Photographic material comprising a support and at least one photographic emulsion layer containing a photographic negative roomlight emulsion, consisting of at least 90 mole % of silver chloride, having an average grain size smaller than 0.3 micrometer, and internally doped with an element of group VIII of the periodic table, characterized in that the emulsion layer further contains an halogen acceptor represented by the following general formula (I):

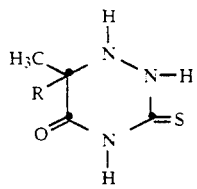
(I)

wherein:
R = alkyl having at least 4 carbon atoms.

2. Photographic material according to claim 1 where, in the general formula (I), R = —$C_6H_{13}$.

3. Photographic material according to claim 1 wherein the halogen acceptor is present in a concentration ranging from $10^{-5}$ to $10^{-2}$ mole per mole of silver halide.

4. Photographic material according to claim 1 wherein the element from group VIII of the periodic table is Rhodium.

* * * * *